(12) United States Patent
Feldman

(10) Patent No.: US 6,572,580 B2
(45) Date of Patent: *Jun. 3, 2003

(54) SET DEPTH NAIL NOTCHER WITH PATCH SYSTEM AND METHOD FOR TREATING NAIL FUNGUS

(75) Inventor: Leonard Feldman, Brooklyn, NY (US)

(73) Assignee: Profoot, Inc., Brooklyn, NY (US)

( * ) Notice: Subject to any disclaimer, the term of this patent is extended or adjusted under 35 U.S.C. 154(b) by 213 days.

This patent is subject to a terminal disclaimer.

(21) Appl. No.: 09/837,343

(22) Filed: Apr. 19, 2001

(65) Prior Publication Data
US 2002/0007191 A1 Jan. 17, 2002

Related U.S. Application Data (63) Continuation-in-part of application No. 09/260,030, filed on Mar. 2, 1999, now Pat. No. 6,264,628, which is a continuation-in-part of application No. 09/129,680, filed on Aug. 6, 1998, now Pat. No. 6,287,276.

(60) Provisional application No. 60/198,576, filed on Apr. 20, 2000.

(51) Int. Cl.[7] ............... A61B 17/20; A61M 37/00
(52) U.S. Cl. ............... 604/46; 604/293; 604/304; 604/500; 606/172; 132/75.4
(58) Field of Search ............... 604/46–47, 48, 604/289–290, 304, 293, 500, 502, 112, 117, 93.01; 606/167, 170–172, 174, 176–177; 128/898; 433/25–26, 30–31, 34, 46; D24/176; 132/76.4, 765, 75.3, 75.4

(56) References Cited

U.S. PATENT DOCUMENTS

| | | |
|---|---|---|
| 678,643 A | 7/1901 | Clarke |
| D35,746 S | 2/1902 | Clark |
| 833,675 A | 10/1906 | Chezem |
| 904,779 A | 11/1908 | Higgins |
| D58,210 S | 6/1921 | Beauregard |
| 1,743,010 A | 1/1930 | Wilmot |
| 2,439,922 A | 4/1948 | Chappell et al. |
| 2,566,688 A | 9/1951 | West |
| 2,573,310 A | 10/1951 | Collier |
| 3,034,507 A | 5/1962 | McConnell et al. |
| 3,600,803 A | 8/1971 | Nachsi |
| 4,005,191 A | 1/1977 | Clark |
| 4,180,058 A | 12/1979 | Brem |
| 5,391,367 A | 2/1995 | DeVincentis et al. |
| 5,422,366 A | 6/1995 | Mintzis et al. |
| 5,437,679 A | 8/1995 | Gaillard |
| 5,464,610 A | 11/1995 | Hayes, Jr. et al. |
| 5,486,537 A | 1/1996 | Farinas |
| 5,573,786 A | 11/1996 | Grabo et al. |
| 5,696,105 A | 12/1997 | Hackler |
| 5,732,719 A | 3/1998 | Godbout |
| 5,879,326 A | 3/1999 | Godshall et al. |
| 5,947,956 A | 9/1999 | Karell |
| 6,042,845 A | 3/2000 | Sun et al. |

FOREIGN PATENT DOCUMENTS

| | | |
|---|---|---|
| SU | 1106495 | 4/1983 |
| SU | 1102592 | 7/1984 |

Primary Examiner—Brian L. Casler
Assistant Examiner—LoAn H. Thanh
(74) Attorney, Agent, or Firm—Stevens, Davis, Miller & Mosher, LLP

(57) ABSTRACT

A kit including a patch laden with topical anti-fungal medication and a set depth nail notcher for cutting a notch of predetermined depth in a nail plate comprising a handle having a smooth flat surface, a longitudinal cutting edge protruding from the smooth flat surface to a height equal to the predetermined depth of the notch. A method for treating nail, especially toenail, fungus comprising cutting a notch to a predetermined depth in a nail or a toe of finger infected with fungus and applying a topical anti-fungal medication to the toe or finger from a patch through the notch.

35 Claims, 5 Drawing Sheets

SET DEPTH NAIL NOTCHER WITH PATCH SYSTEM AND METHOD FOR TREATING NAIL FUNGUS

This is a continuation-in-part of U.S. patent application Ser. No. 09/260,030, filed Mar. 2, 1999 (now U.S. Pat. No. 6,264,628 B1, which is a continuation-in-part of U.S. patent application Ser. No. 09/129,680, filed Aug. 6, 1998.

This claims priority from U.S. provisional patent application No. 60/198,576, incorporated herein by reference.

BACKGROUND OF THE INVENTION

1. Field of the Invention

The present invention relates to a system including a nail notcher for cutting a notch in a nail plate and a patch to assist in holding anti-fungal medication in place. The present invention also relates to a method for applying topical anti-fungal composition to fungus underneath a nail by applying the composition through the notch cut by the nail notcher of the present invention and placing a patch over the notch to assist in holding the anti-fungal medication in place.

2. Background Discussion

A human's nail has a nail plate, which is a hard outer surface of dead cells, and a nail bed below the nail plate. The nail plate is non-porous, whereas the nail bed is porous. There is soft flesh beneath the nail bed. The nail plate and the nail bed are relatively insensitive to pain. The underlying flesh is sensitive to pain. The nail plate, nail bed, and, in severe cases, the flesh below the nail bed can be infected by a wide variety of common fungi. Such fungi are responsible for nail infections, medically known as onychomycosis. Examples of onychomycosis are caused by fungi, such as trichophyton mentagrophytes, candida albicans or trichophyton rubrum. Other terms for onychomycosis are ringworm of nails or tinea unguium.

It is difficult to treat such infections. Although the infections are highly localized, they are located in a part of the body which is difficult to reach. U.S. Pat. No. 5,573,786 discloses application of the composition for treating fungal diseases of the skin and mucus membrane with a small, pointy wooden stick or thin plastic porous plastic stick, or brush for treating large areas. Its Example 11 discloses onychomycosis treatment of a fingernail. However, the Example emphasizes that its preparation is suitable for treating superficial onychomycotic infections. In the case of infection of the nail bed, however, therapy must be carried out together with an oral antimycotic. U.S. Pat. No. 5,573,786 is incorporated herein by reference.

U.S. Pat. No. 5,696,105 discloses drilling holes in nails to apply anti-fungal medication, as an attempt to improve topical administration of medication. U.S. Pat. No. 5,696,105 also discloses other local measures to treat nail fungus include mechanical ablation of affected nail areas, or nail removal. U.S. Pat. No. 5,696,105 is incorporated herein by reference. U.S. Pat. No. 5,696,105 also discloses application of anti-fungal medication with a brush or an applicator tipped bottle.

Rather than directly applying topical anti-fungal medication, systemic treatments are also employed. However, such systemic treatments spread medication throughout the patient's body. Thus, the medicine is not concentrated in the infected area and may cause side-effects.

It would be desirable to provide a medication for treating nail fungus, particularly toenail fungus, which easily can be directly applied to the nail to result in effective, painless and bloodless treatment.

SUMMARY OF THE INVENTION

It is an object of the invention to provide a system including a set depth nail notcher for cutting a notch in a fingernail or toenail plate.

It is another object of the invention to provide a method for applying topical anti-fungal medication to an infected nail area through a notch cut in the nail plate by the set depth nail notcher of the present invention and placing the patch impregnated with or otherwise containing anti-fungal medication over the notch.

In its apparatus respects, the present invention relates to a system including a set depth nail notcher for cutting a notch of predetermined depth in a fingernail or a toenail plate and a patch for holding anti-fungal medication in place and delivering the medication to the notch and underlying tissue. The nail notcher comprises a handle having a smooth flat surface and a longitudinal cutting edge protruding from the smooth flat surface. The longitudinal cutting edge protrudes from the smooth flat surface to a height equal to the predetermined depth of the notch. If desired, the set depth nail notcher may provide a smooth convex surface rather than a smooth flat surface for a cutting edge to protrude therefrom. The patch is an adhesive patch including a portion for being impregnated with or otherwise contain anti-fungal medication and a flexible adhesive portion bordering the portion for being impregnated. Any pad which is capable of holding the mediation is suitable for the portion for being impregnated. Typically the pad is supple and the adhesive portion is flexible such that the patch will conform to the shape of the toe, finger and/or nail to which it is applied.

The patch serves to protect the open notch from contamination as well as prevent loss of the medication. Thus, it is easy for the patient to apply the medication to the notch and by virtue of the patch, maintain a normal daily routine while the medication is in the notch and underlying tissue. This easily permits extended treatment times. The patch may be particularly effective for time release formulations of anti-fungal medication.

In its method respects, the present invention involves a method for treating fingernail or toenail fungus comprising employing the above-described nail notcher to cut a notch to a predetermined depth in a fingernail or a toenail infected with fungus. Then a topical anti-fungal medication is applied to the nail bed of the finger or toe through the notch cut by the above-described nail notcher. As many as two or three notches may be employed on each nail. The medication may be put on/into the patch before the patch is put on the notch, or the medication may be put on/into the notch before the patch is put on the notch.

The method treats the infected nail to create a sterile antiseptic area proximal to the cuticle of the infected nail. Then the infected area grows distally away from the cuticle and is eventually trimmed off. The sterile area typically extend into the nail bed and may extend into the underlying flesh.

BRIEF DESCRIPTION OF THE DRAWINGS

The present invention is illustrated by the below-described drawings, wherein like elements are labeled with like numerals.

DETAILED DESCRIPTION OF THE PREFERRED EMBODIMENTS

The nail notching device (NND) is designed to assist a patient, doctor, or technician in manually abrading a recessed notch or groove in either the toe or finger nail plate. A purpose of this notch is to allow a contemporaneous application of over-the-counter (or prescription) topical antifungal liquid, e.g., solution, gel or cream access to the soft tissue of the nail bed below the nail plate.

Figures 1, 2:
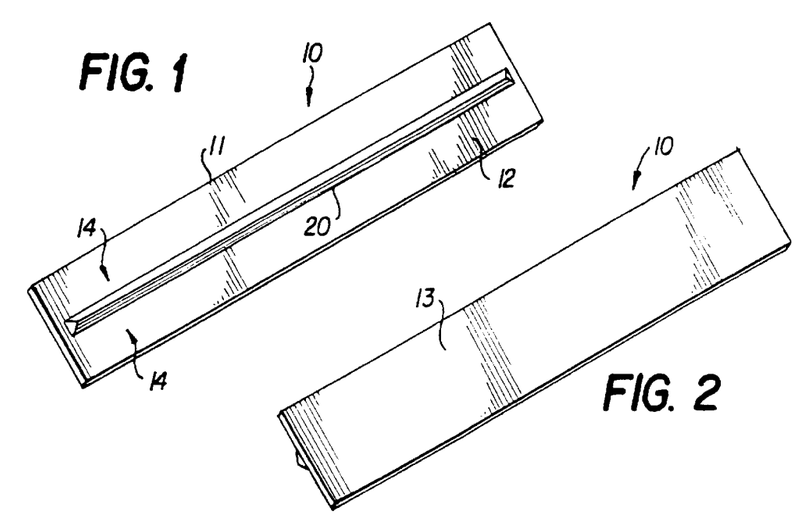
FIG. 1 discloses a perspective bottom view of the first embodiment of the present invention.
FIG. 2 discloses a perspective top view of the embodiment of FIG. 1.

FIG. 1 shows a first embodiment of a nail notcher 10 of the present invention. The nail notcher 10 has a file pad 11 (as a substrate) and a cutting edge 20. The file pad 11 has a smooth flat bottom surface 12 and a smooth, flat top surface 13 (FIG. 2). The cutting edge 20 protrudes from the smooth, flat bottom surface 12. The cutting edge 20 may be attached to or integral with the file pad 11. The file pad 11 is elongate and thus has a longitudinal axis. Thus, the cutting edge 20 is also longitudinally arranged relative to the file pad.

Figure 3:
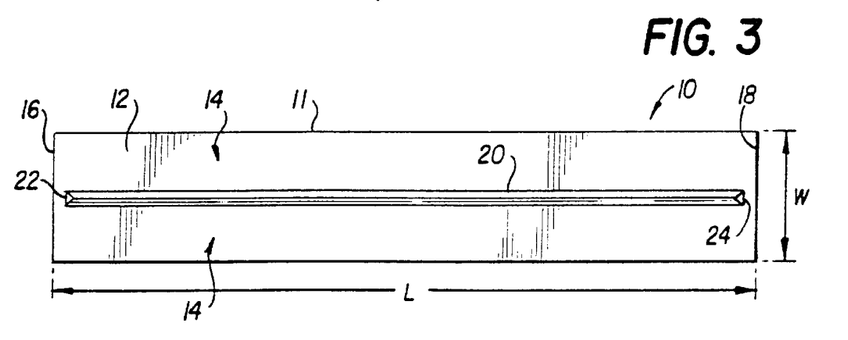
FIG. 3 discloses a bottom view of the embodiment of FIG. 1.
Figure 4:
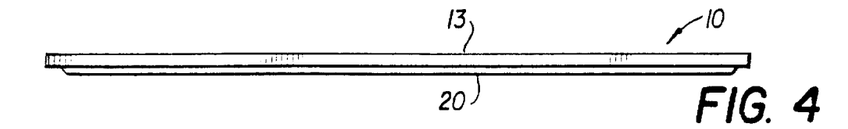
FIG. 4 discloses a side view of the embodiment of FIG. 1.

As shown in FIG. 3, the file pad 11 has a first end 16 and a second end 18. Likewise, the cutting edge 20 has a first end 22 and a second end 24. The first end 22 of the cutting edge 20 may be at or adjacent the first end 16 of the file pad 11. The second end 24 of the cutting edge 20 may also be at or adjacent to the second end 18 of the file pad 11. FIG. 3 shows first end 22 of the cutting edge 20 being adjacent the first end 16 of the file pad 11. FIG. 3 also shows the second end 24 of the cutting edge 20 being adjacent the second end 18 of the file pad 11. (Of course, although not shown, the cutting edge ends may extend to the file pad ends.)

Figure 6:
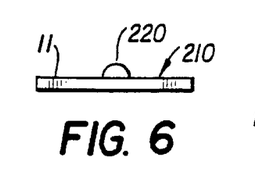
FIG. 6 discloses a front view of a third embodiment of the present invention.
Figures 7, 8:
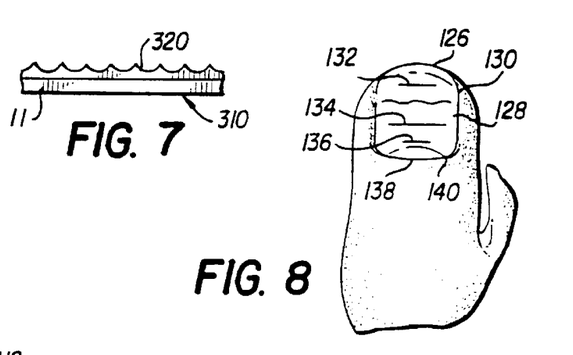
FIG. 7 discloses a partial side view of a fourth embodiment of the present invention.
FIG. 8 discloses an infected toenail being treated according to the present invention.
Figure 9:
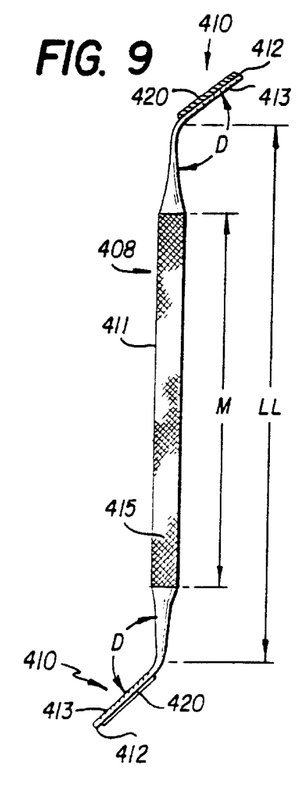
FIG. 9 is a side view of a third embodiment of a nail notching device of the present invention.

By definition in this disclosure, the cutting edge 20 includes edges which cut by sharpness or by abrasion. The cutting edge 20 may contain a straight edge, abrasive or saw-toothed (notched) edge which is capable of penetrating the nail plate to expose the nail bed. In particular, the edge may be a sharp straight edge (as shown in FIG. 3) or round (as shown in FIG. 6) or serrated (as shown in FIG. 7) to expose the maximum area of the nail plate for maximum penetration of medication. The nail notcher 10 is capable of producing an exact depth notch limited by the depth of the cutting edge 20 and the smooth shoulders 14 on either side of the cutting edge 20.

For example, the cutting edge 20 may have a depth of about 0.5 to about 4 mm, preferably about 1 to about 4 mm, and more preferably about 1 to about 3 mm.

Figure 5:
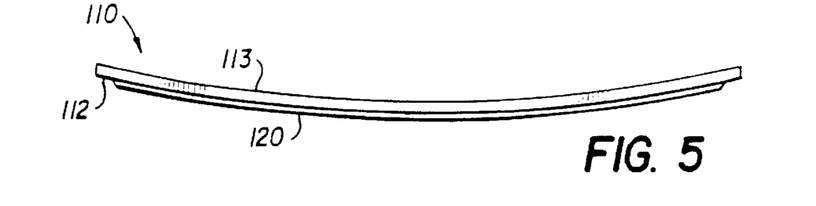
FIG. 5 discloses a side view of a second embodiment of the present invention.

The nail notcher 10 is typically made of a material able to be autoclaved or sanitized. For example, the file pad 11 may be made of metal or plastic. The cutting edge 20 is made of metal or any other material suitable for cutting. Also, combinations such as laminates of metal or plastic are possible for the file pad 11. The nail notcher 10 can either be a flat nail notcher 10 (as shown in FIGS. 1–4) or be a curved nail notcher 110 (the second embodiment as shown in FIG. 5) or other convenient shape which provides shoulders. The nail notcher 10 typically has a surface length "L" (FIG. 3) of from about 1 to about 5 inches. The nail notcher 10 also has a width "W" of from generally about 3/8 inch to about 1 inch. In general, the nail notcher 10 is sized for easy gripping and use. Thus, it may be provided with additional features to facilitate gripping and use, such as clamps or one or more protrusions from the upper surface or the nail handle may have contoured side edges, etc.

FIG. 5 shows a second embodiment of the nail notcher 110 of the present invention having a smooth continuous convex surface 112 from which a cutting edge 120 protrudes. Curved nail notcher 110 also has a concave top surface 113. However, if desired, the top surface may be flat even though the opposed surface 112 is convex.

FIG. 6 shows a third embodiment of a nail notcher 210 of the present invention having a file pad 11 as in the first embodiment of FIG. 1, but provided with a rounded cutting edge 220 having an abrasive surface of abrasive material conventionally employed with nail files or a rough metal surface. This embodiment is advantageous because it cuts a wider groove in the nail than would a sharp edge. This wide groove is advantageous because it exposes more nail bed area for applying the topical medication. Although not required, the groove may be wider than it is deep.

FIG. 7 shows a side view of a fourth embodiment of the present invention of a nail notcher 310 having a handle 11 provided with a serrated cutting edge 320.

Any of the above nail notchers may be employed to treat nail fungus. Typically, a nail notcher, such as nail notcher 10, would be employed as follows. A patient or medical professional would rub the cutting edge of the nail notcher on a nail to abrade the nail plate to a prescribed depth. The abrading of the nail plate would occur by rubbing the surface of the nail with the nail notcher 10 until the cutting edge penetrates sufficiently deep into the nail for the smooth flat bottom surface 12 to contact the nail bed. In some instances, two or three notches may be made in the same nail for application of medication to multiple locations. In other instances, one notch may suffice. The notch (or notches) should expose the nail bed below the hard outer surface of the nail for subsequent application of topical anti-fungal medication which is then absorbed and, preferably, permeates the nail bed. The nail bed is the soft porous layer of the nail between the nail plate and the flesh below the nail.

The smooth flat bottom surface 12 prevents the cutting edge from cutting too deeply into the nail. Thus, the cutting edge 20 cuts into the nail bed and may cut to, but preferably not through, the underlying flesh. If the flesh is contacted, the contact is slight and does not cause bleeding. Thus, the present method is a bloodless procedure. Due to the porous nature of the nail bed, the notch may be sufficiently deep for applying medication for treating fungus without contacting the underlying flesh. This is particularly the case where the flesh is not infected.

Although a smooth flat bottom surface 12 is disclosed, any surface which provides depth stopping surface along at least one side of the length of the cutting edge 20 may be employed. For example, the bottom surface may comprise ribs (not shown) parallel to the cutting edge 20 to control cutting depth.

If the initially employed nail notcher does not cut a notch sufficiently deep to penetrate the hard outer surface of the nail, then a nail notcher having a cutting edge to provide a deeper cut than the already used nail notcher would be employed.

After cutting the appropriate notch or notches, a topical anti-fungal medication would be applied through the notch or notches. The medication could be any of the FDA (Food and Drug Administration) approved over-the-counter or prescription anti-fungal medications already in use. The topical medication would be placed into the notch (or notches) and then diffuse through the nail bed into the infected area under the nail. Typical anti-fungal medications which may be employed with the nail notcher 10 of the present invention include chlortrimizol, tolnaftate and undecylenate acid.

In addition to the active ingredient, pharmaceutically acceptable adjuvants, stabilizers, preservatives, whiteners, buffers and surfactants may be used in the formulations employed with the present invention. The antifungal composition may be in the form of liquid, e.g., solution, gel, semi-solid, cream or solid. It also may be applied as one form, e.g., liquid, which then converts, e.g., dries, to another form, e.g., solid.

Thus, the present invention penetrates the nail plate to expose the nail bed, by an exact depth notch limited by the depth of the cutting edge and the shoulders on either side of the sharp or abrasive edge to facilitate treatment.

For example, as shown in FIG. 8, notches 132, 134, 136 are cut with nail notcher 10 into a toenail 128. FIG. 8 shows fungus infecting a distal region 130, relative to the cuticle 138, of the toenail 128. Notch 132 is cut into the infected region 130 in a direction transverse to a longitudinal direction of the toe nail 128. The longitudinal direction being the direction from the cuticle 138 to the distal end of the nail. Notches 134, 136 are cut into an uninfected region 140 of the nail 128 which is proximal to the cuticle 138. In severe cases all the notches may be cut into an infected portion of nail because little or no uninfected portion is accessible. In some instances the toenail 128 may be filed to smooth its surface prior to cutting the notches into the surface.

After the notches are cut, at least one medicine which is a fungicide (kills fungus) or a fungistat (prevents fungus growth) is applied to the notches 132, 134, 136. The notches 132, 134, 136 are cut sufficiently deep to cut into the bed of the nail 128. Thus, the medication passes into the notches 132, 134, 136 and through the nail bed. This creates a sterile antiseptic area under the treated portions of the nail, especially for the proximal region 140. As noted above, the medicine may not kill fungus. However, it at least prevents its growth. Thus, the treatment prevents the fungus in the infected portion 130 from spreading to the uninfected portion 140. Then antifungal medicine is routinely reapplied to the notches for a sufficient number of days or weeks. During this treatment time, the nail continues to grow and the infected portion 130 grows distally away from the cuticle 138 and is eventually trimmed off to remove the infection from the patient.

Figures 10, 11, 13:
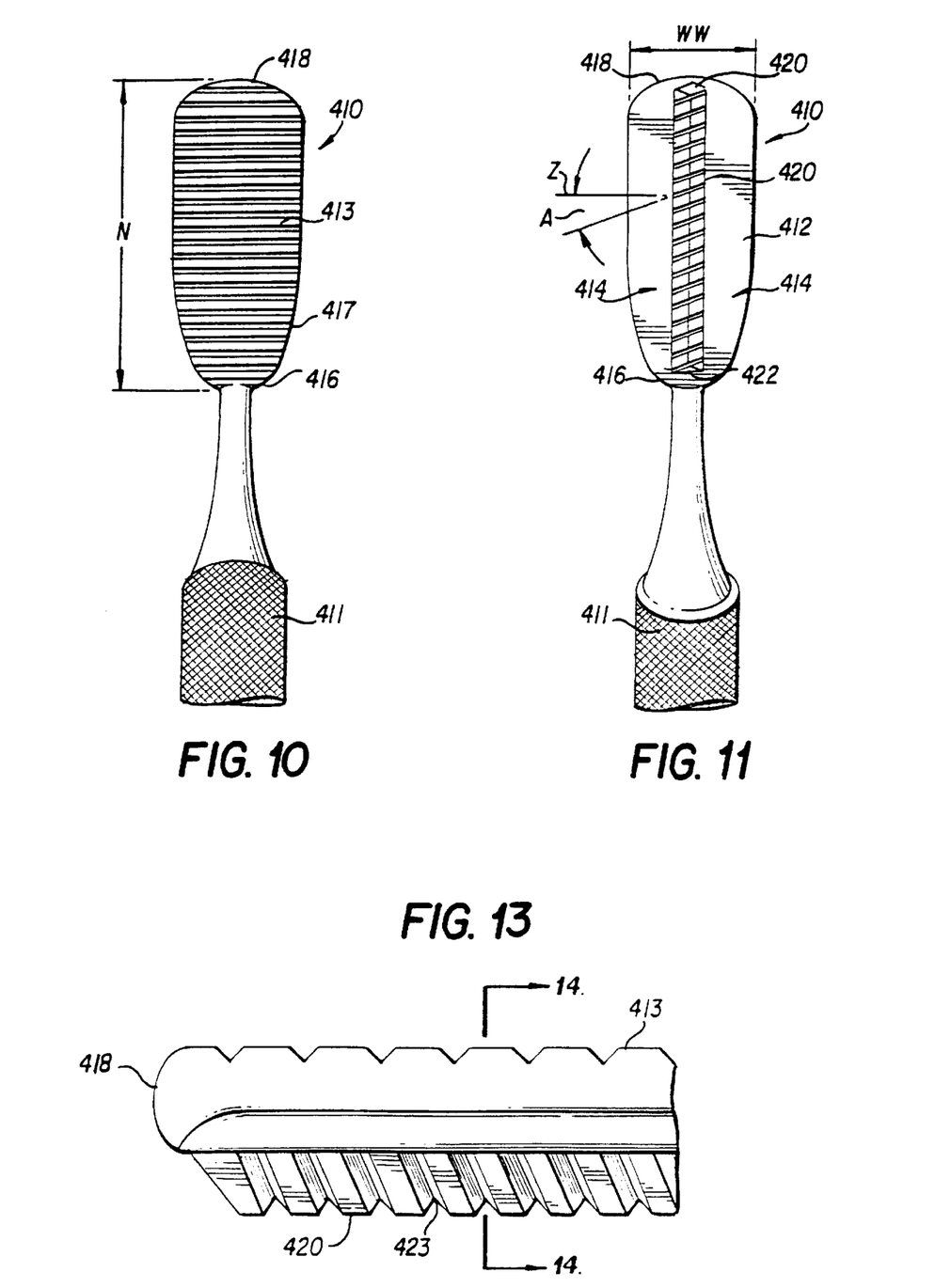
FIG. 10 is an enlarged view of the top side of a file pad of the embodiment of FIG. 9.
FIG. 11 is an enlarged view of the bottom side of a file pad of the embodiment of FIG. 9.
FIG. 13 is a side view of a portion of a file edge of a file pad of the embodiment of FIG. 9.

FIGS. 9–17 show another embodiment of a nail notcher device 208 useful in the present invention. The nail notcher device 408 (FIG. 9) is a hand-held, one-piece tool preferably constructed of milled stainless steel. There is an elongated center handle grip 411 with angled file pads 410 at either end. Preferably, the elongated center handle grip 411 has a knurled surface 415. These file pads 410 are designed and precision milled to abrade a precise depth notch in the hard nail plate exposing the nail bed, while minimizing the risk to soft tissues. The file pads 410 have a smooth bottom surface 412 and a top grip surface 413. Each file pad 410 has a first end 416 and a second end 418 (FIG. 11). The top grip surface 413 may be any suitable surface, smooth or rough, i.e., textured. However, preferably it is rough. For example, FIG. 10 shows top grip surface 413 having channels 417. Each file pad 410 includes a bottom surface 412 having a smooth polished surface (shoulder 414) with a raised latitudinal file edge 420 as a serrated cutting edge running down the center. File edge 420 is latitudinal relative to the handle grip 411 but longitudinal relative to the respective file pad 410. The file edges each have a first end 422 and a second end 424. The file edges 420, rise to prescribed heights above smooth surface 412 and will abrade the nail plate to the equivalent depth. File edges 420 have peaks 425 of height "B", and intermediate valleys 423 of height "C". Each file edge 420 may have the same or different dimensions, e.g., heights, lengths or widths, relative to the other file edge 420. Moreover, each file edge 420 may be made of the same or different materials relative to the other file edge 420.

Figure 16:
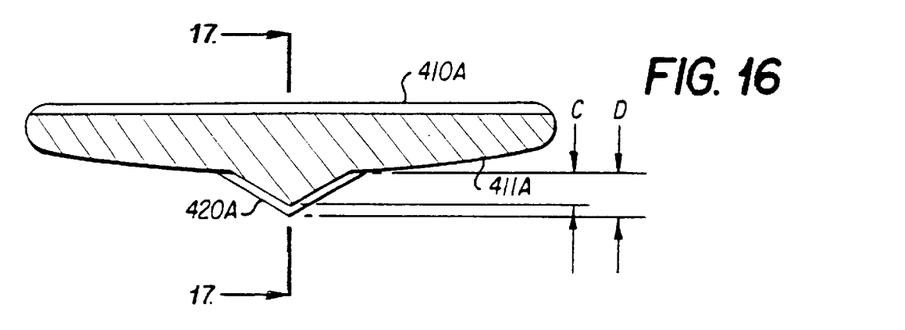
FIG. 16 is a cross-sectional front view of the file pad of FIG. 13 modified to have a cutting edge having a different height.
Figure 17:
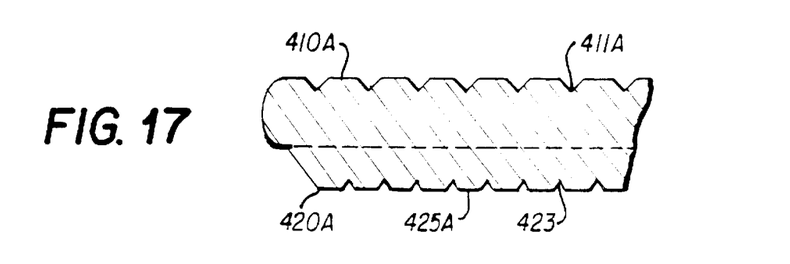
FIG. 17 is a cross-sectional side view of the file pad of FIG. 16.

For example, one end of the grip 411 may have file pad 410 while the other end of the grip 411 has file pad 410A which is the same as file pad 410 except for having an edge 420A which has a different peak height "D" (FIG. 16). Heights B, D typically range from about 0.5 mm to about 4 mm, preferably about 1 mm to about 4 mm, or more preferably about 1 mm to about 3 mm. These heights are suitable for a human nail. Height "C" typically ranges from about 0.25 mm to about 2 mm less than the respective height B, C. The angle "A" of the valleys 423 between the peaks of edges 420 or 420A generally range from 0° to about 80°, preferably from 0 to about 45°. Angle "A" is defined as the angle formed by a line passing through the valley 423 and a line "Z" which is normal to the file edge 420 and transverse to one of the shoulders 214.

The file edge 420 as shown is metal cut with valleys 423 to form a file surface. However, an abrasive-coated edge would also provide a file edge. If desired, a sharp cutting edge could be substituted for the file edge 420.

The angle "D" between the file pads 410 and the elongated center handle grip 411 generally ranges from about 90° to about 180°, preferably about 100° to about 170°.

The length "LL" of the elongated center grip 411 generally ranges from about 2 inches to about 6 inches. The length "M" (FIG. 9) of the knurled surface 415 generally ranges from about 1.5 to about 5 inches. The length "N" (FIG. 10) of the file pads 410 generally ranges from about 0.375 inch to about 1 inch. The width "WW" of the file pads 410 generally ranges from 0.25 inch to about 1 inch. For example, the two file edges 420, 420A may have respective heights B, D of 1.2 mm and 1.8 mm.

The smooth shoulders 414, from which the file edges 420, 420A rise substantially perpendicularly, will prevent the file edges 420, 420A from notching deeper into the nail by making solid contact with the nail surface on either side of the notch.

Figure 12:
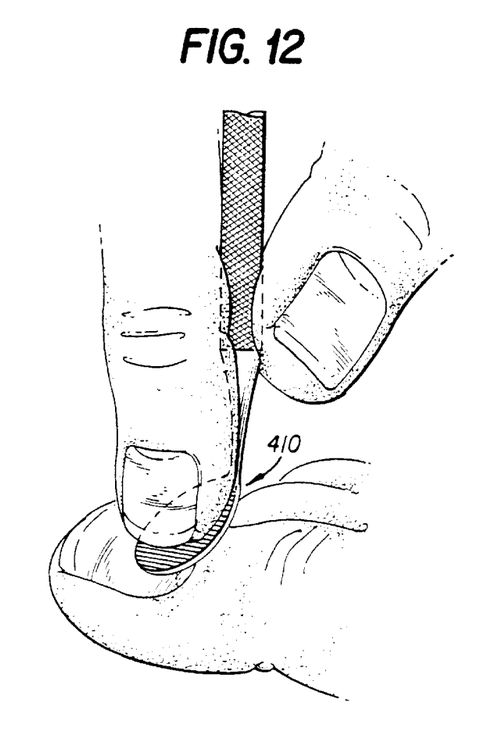
FIG. 12 is an enlarged view of the nail notching device of FIG. 9 in use.
Figure 14:
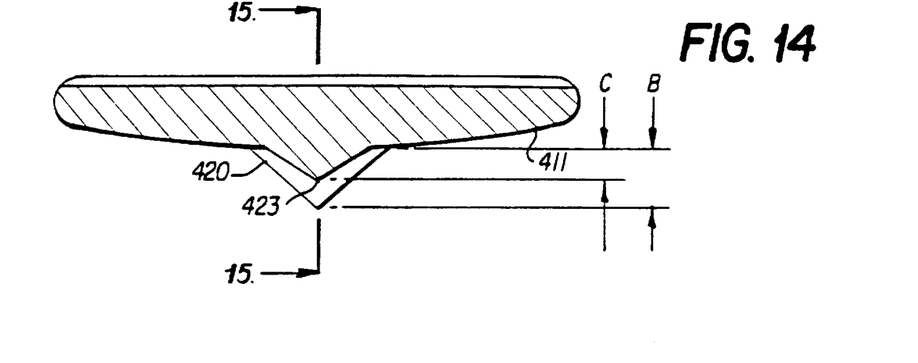
FIG. 14 is a cross-sectional front view of the file pad of FIG. 13.
Figure 15:
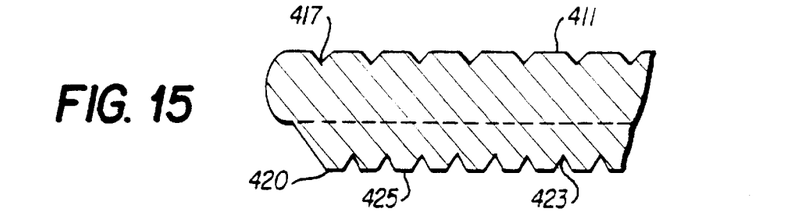
FIG. 15 is a cross-sectional side view of the file pad of FIG. 13.

The nail notching device 408 is designed to be extremely easy and safe to use. Its design renders the device virtually mistake-proof. Subjects simply place the prescribed file pad on the desired nail area and file a transverse notch with a simple "back and forth" motion (FIG. 12). Its operation is as simple and requires as much effort as a common nail file. The file edge is finely milled, and requires a minimal amount of pressure to abrade a precise notch. Additionally, the elongated handle makes the nail notching device 408 easier for toenail applications where excessive stretching or reaching may cause discomfort.

Due to the inherent properties of the file edge and simplicity of design, the nail notching device presents no major risk of injury even for use by the general public. The ergonomic design, rounded edges, and positive grip minimize the risk of injury due to slippage. The self limiting file edge prevents any possibility of a deep wound or "overnotching", and the abrasive edge is not sharp enough to lacerate skin or soft tissue easily. The nail notching device 408 is sturdily constructed of one continuous piece of high quality stainless steel and presents a minimum risk of spreading infection. Prior to use, subjects would be instructed on how to clean and sterilize the nail notching device. Subjects should not share device with others.

Conveniently, the nail notcher/patch system may be provided as a kit. The nail notcher being as described above. The anti-fungal medication may be an ointment, a liquid, a paste, or a gel. Many suitable medications are already on the market. The medication may be in the form of a sustained release formulation. The composition of such a suitable sustained release formulation would be known to those skilled in the art.

If the patch is impregnated prior to use, then it is sold in a sealed package (not shown) to prevent degradation of the medication. An example of a suitable package to protect the patch would be the foil packs typically used for pre-moistened towelletts.

If the patch is impregnated during use, then it could be sold in a kit containing the notcher, the patch packaged to keep it dry, clean and sterile, as well as a tube of anti-fungal medication. Suitable packaging for a dry patch could be such as that used to package BAND-AID brand adhesive bandage strip.

If desired, the medication may be applied to the notch and then a patch, such as an appropriately shaped BAND-AID brand adhesive bandage strip, applied over the medicated notch.

The application of the medication similar to that of transdermal drug delivery systems may be employed. For example, delivery by diffusion would occur by simply placing a high dose of medication in the patch, applying the patch to the notch, and then allowing the medication to pass into the notch to diffuse through the nail bed to the tissue therebelow. Delivery by diffusion would also occur by simply placing a high dose of medication in the notch, applying the patch to the notch, and then allowing the medication from the notch to diffuse through the nail bed to the tissue therebelow.

A transdermal system for delivering nicotine, not anti-fungal medication, is disclosed by U.S. Pat. No. 4,597,961 to Etscorn, incorporated herein by reference. Such a system could be modified to deliver anti-fungal medication. Thus, a patch for administering anti-fungal medication would typically comprise an occlusive pad which is capable of adhering to the skin/nail and administering a dosage rate sufficient to treat the fungus. The occlusive pad comprising an anti-fungal medication-impermeable backing and an anti-fungal-medication permeable, porous, inert membrane. The anti-fungal medication-impermeable backing and anti-fungal-medication permeable, porous, inert membrane defining a cavity therebetween. The cavity containing a liquid anti-fungal medication.

Figure 19:
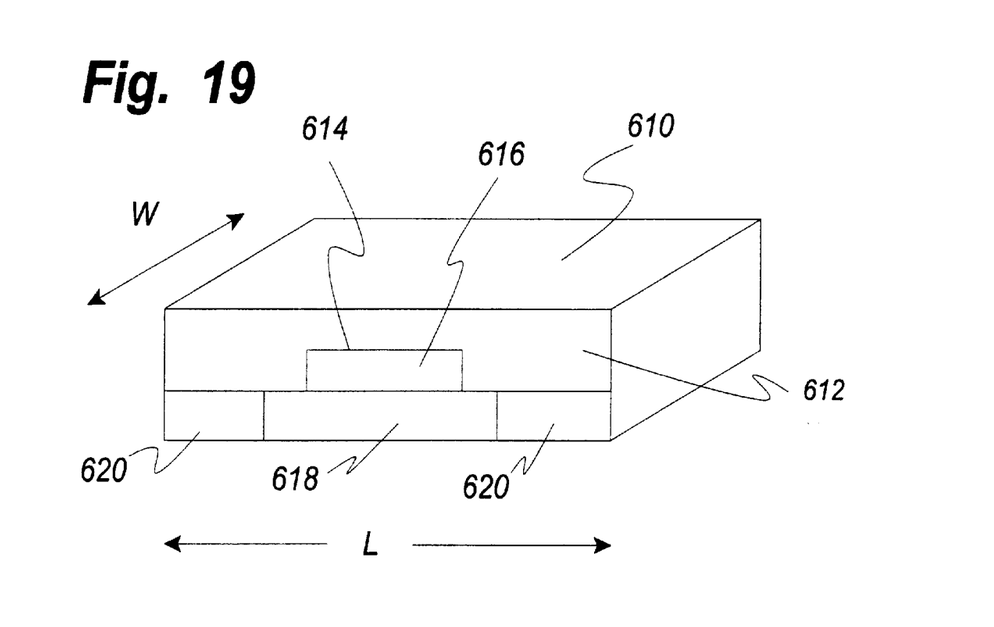
FIG. 19 shows another embodiment of a typical patch which may be employed with the present invention.

A typical such bandage is shown in FIG. 19. The bandage 610 has a width of about 0.5 to 2 centimeters and a length of about 0.75 to 3centimeters. It comprises an anti-fungal medication impermeable backing 612 formed of a suitable, preferably flexible and impervious plastic or rubber material such as a polyvinylidene chloride, polyethylene, polypropylene, nylon, silicone rubber, etc., having a cavity 614 along one surface thereof. Within the cavity 614 is provided a suitable amount of liquid anti-fungal medication 616. Sealing the medication is a film 618 again formed of a suitable microporous and flexible plastic or rubber which is inert to the medication. A suitable adhesive 620 is provided on either side of, or completely around the medication permeable membrane.

The nature of the materials from which the bandage 610 may be formed are readily determinable from the below mentioned U.S. Pat. Nos. 3,598,122 and 3,948,254 to Zaffaroni, coupled with routine testing to confirm the materials are inert to the medication. The bandage 610 may be kept sealed in an air tight pouch prior to use to prevent drying out of the bandage or other undesirable consequences. If desired, a suitable absorbent material, such as cotton or sponge (not shown) may be in the cavity and impregnated with the material.

Other patents which disclose bandages for administering pharmaceuticals transdermally through the skin include U.S. Pat. Nos. 3,598,122 and 3,948,254 to Zaffaroni incorporated herein by reference. These bandages may be modified to apply topical anti-fungal medication to a nail notch.

Figure 18:
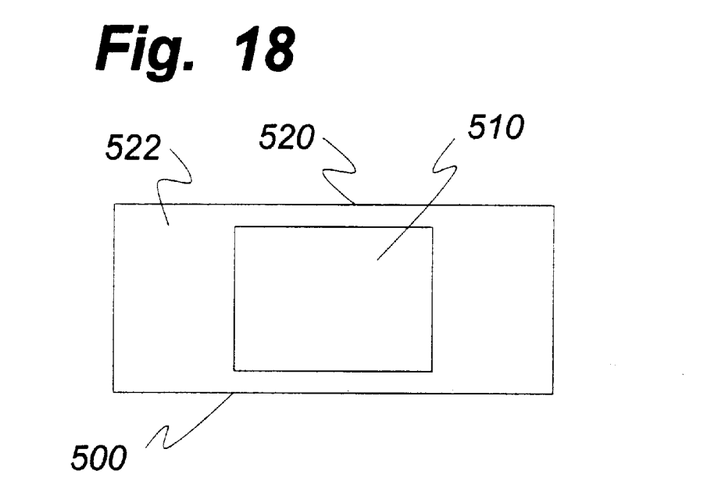
FIG. 18 shows an example of a typical impregnated bandage that may be employed with the present invention.

FIG. 18 shows an example of a typical impregnated bandage 500 having a gauze pad 510 and a flexible portion 520 having an adhesive coated surface 522. Typical flexible portions 520 are made of polymer. However, any suitable bandage or tape may be employed. The adhesive coating may be any coating used to removably adhere to skin for bandages. Portions of the flexible portion 520 extend from opposed sides of the pad 510. Typically, the pad and the adhesive portion can bend such that the patch 500 will conform to the shape of the toe, finger and/or nail to which it is applied.

The present invention is a major advance in treating nail, especially toenail, fungus because it provides for an easy to make, safe, and not too deep, notch into the nail bed. This makes it easy and relatively painless for patients to treat themselves or be treated by a physician or nurse. Also, to apply the topical antifungal medication directly to the nail bed is a major advance. This will make the topical antifungal medications already on the market more effective because they will now directly, contact the nail bed and permeate into the nail bed. Moreover, covering the medicated notch with a patch will protect the medication to permit it to be effective over long periods of time.

The patch serves to protect the open notch from contamination as well as prevent loss of the medication. Thus, it is easy for the patient to apply the medication to the notch and by virtue of the patch, maintain a normal daily routine while the medication is in the notch and underlying tissue. This easily permits extended treatment times. The patch may be particularly effective for time release formulations of antifungal medication.

It should be apparent that embodiments other than those specifically described above come within the spirit and scope of the present invention. Thus, the present invention is not limited by the above-described embodiments, but rather by the claims appended hereto.

What is claimed is:

1. A system comprising:
a patch containing a topical antifungal medication; and
a set depth nail notcher for cutting a notch of predetermined depth in a nail plate comprising:
at least one substrate having an upper surface and a bottom surface;
an elongate longitudinal cutting edge means for rubbing back and fourth protruding from the respective bottom surface to a height for cutting the predetermined depth of the notch, wherein at least a portion of the bottom surface provides a surface to prevent the cutting edge from cutting deeper than the predetermined notch depth, wherein the cutting edge protrudes from the bottom surface to a height equal to the predetermined depth of the notch, wherein the notch depth is sufficient to cut through a nail plate of the nail into a nail bed under the nail plate.

2. The system of claim 1, wherein the patch comprises an adhesive portion and a portion containing the topical antifungal medication.

3. The system of claim 1, wherein the longitudinal elongate cutting edge means has longitudinal sides and is located on the bottom surface to define two smooth shoulders of surface, each shoulder being lateral to one longitudinal side of the cutting edge.

4. The system of claim 1, wherein the patch contains a composition for sustained release of the topical antifungal medication.

5. The system of claim 1, wherein the anti-fungal medication is at least one composition selected from the group consisting of an ointment, a paste, a gel, and a liquid.

6. The system of claim 1, wherein the cutting edge means comprises an abrasive surface.

7. The system of claim 1, wherein the cutting edge means comprises serrated metal.

8. The system of claim 1, wherein the cutting edge means comprises a straight edge.

9. The system of claim 1, wherein the cutting edge means comprises a file edge.

10. The system of claim 1, further comprising an elongated center handle having two ends,
wherein at least one of said handle ends has one said substrate respectively attached thereto and optionally the other handle end has another substrate respectively attached thereto.

11. The system of claim 1, wherein the patch comprises a gauze pad impregnated with the topical antifungal medication and attached to an adhesive strip, and portions of the adhesive extend from at least two opposed sides of the gauze pad.

12. The system of claim 1, wherein said cutting edge means protrudes from said bottom surface about 0.5 mm to about 4 mm.

13. The system of claim 1, wherein said cutting edge means protrudes from said bottom surface about 1 mm to about 4 mm.

14. A method for treating fungus comprising:
cutting an elongate continuous notch to a predetermined depth in a nail selected from the group of a toenail and a fingernail infected with fungus by rubbing a set depth nail notcher on a nail plate of the nail, the nail notcher comprising:
a substrate having an upper surface and a bottom surface;
an elongate cutting edge protruding from the bottom surface to a height of the predetermined depth of the notch;
applying a patch containing topical anti-fungal medication to the toenail or fingernail through the notch, wherein said predetermined depth is sufficient to penetrate the nail plate and contact the nail bed;
wherein at least a portion of the cutting edge is rubbed on the nail in a direction along a longitudinal axis of the cutting edge.

15. The method of claim 14, and further wherein the cutting edge is cut through the nail plate but does not contact tissue under a nail bed of the nail.

16. The method of claim 15, wherein the patch comprises an adhesive portion and a portion containing the topical antifungal medication.

17. The method of claim 15, wherein the cutting edge has longitudinal sides and is located on the bottom surface to define two smooth shoulders of surface, each shoulder being lateral to one longitudinal side of the cutting edge, further comprising rubbing at least a portion of each shoulder on the nail.

18. The method of claim 15, wherein the patch contains a composition for sustained release of the topical antifungal medication.

19. The method of claim 15, wherein the anti-fungal medication is at least one composition selected from the group consisting of an ointment, a paste, a gel, and a liquid.

20. The method of claim 15, wherein the patch comprises a gauze pad impregnated with the topical antifungal medication and attached to an adhesive strip, and portions of the adhesive extend from at least two opposed sides of the gauze pad.

21. The method of claim 15, wherein the cutting edge comprises an abrasive surface, wherein the cutting edge abrades the nail during said cutting.

22. The method of claim 15, wherein the cutting edge comprises serrated metal.

23. The method of claim 15, wherein the cutting edge comprises a straight edge.

24. The method of claim 15, wherein the set depth nail notcher further comprises an elongated center handle, for being gripped by a user, having first and second handle ends,
wherein said substrate is extending from said first handle end, and
said notcher optionally having a second file pad extending from said second end, said second file pad having an upper surface and a bottom surface; wherein a second elongate cutting edge protrudes from the bottom surface of the second substrate to a height for cutting the predetermined depth of the notch.

25. The method of claim 15, wherein each handle end is attached to a respective said substrate.

26. The method of claim 15, wherein the cutting edge is a file edge.

27. The method of claim 14, wherein the notch is cut into a bed of the nail and the topical anti-fungal medication diffuses from the notch into the nail bed to contact flesh under the nail.

28. The method of claim 14, wherein the topical antifungal medication comprises a least one member selected from the group consisting of a fungicide and a fungistat.

29. The method of claim 14, further comprising a step of trimming an infected portion of the nail away from the nail after application of the topical anti-fungal medication.

30. The method of claim 14, wherein the notch is a rounded groove.

31. The method of claim 14, wherein the notch is formed by rubbing the cutting edge against the nail in a back and forth motion along a direction transverse to the direction in which the nail grows, forming the notch removes a portion of the nail, and the notch is formed to be transverse to the direction in which the nail grows.

32. The method of claim 14, wherein the height the cutting edge protruded from the first surface is constant.

33. A method for treating fungus comprising:

cutting an elongate continuous notch to a predetermined depth in a nail selected from the group of a toenail and a fingernail infected with fungus by rubbing a set depth nail notcher on a nail plate of the nail, the nail notcher comprising:

a file pad having an upper surface and a bottom surface;

an elongate cutting edge protruding from the bottom surface to a height of the predetermined depth of the notch;

applying a topical anti-fungal medication to the toenail or fingernail through the notch, wherein said predetermined depth is a depth from 0.5 mm to 4 mm.

34. The method of claim 33, wherein the notch is formed by rubbing the cutting edge against the nail in a back and forth motion along a direction transverse to the direction in which the nail grows, forming the notch removes a portion of the nail, and the notch is formed to be transverse to the longitudinal direction of the nail.

35. The method of claim 33, wherein said predetermined depth is a depth from about 1 mm to about 4 mm.

* * * * *